United States Patent [19]
Takahashi et al.

[11] Patent Number: 4,942,867
[45] Date of Patent: Jul. 24, 1990

[54] DISTAL END PART OF ENDOSCOPE

[75] Inventors: Nagashige Takahashi; Teruo Ouchi, both of Tokyo, Japan

[73] Assignee: Asahi Kogaku Kogyo K.K., Tokyo, Japan

[21] Appl. No.: 376,625

[22] Filed: Jul. 7, 1989

[30] Foreign Application Priority Data

Jul. 13, 1988 [JP] Japan ................................. 63-176081
Jul. 22, 1988 [JP] Japan ................................. 63-183955

[51] Int. Cl.$^5$ .............................................. A61B 1/06
[52] U.S. Cl. ......................................................... 128/6
[58] Field of Search ..................................... 128/6, 7, 4

[56] References Cited

U.S. PATENT DOCUMENTS 4,500,181  2/1985  Takahashi ........................ 128/6 X
4,562,831  1/1986  Murakoshi et al. ..................... 128/6

FOREIGN PATENT DOCUMENTS

414670  3/1941  Japan.

Primary Examiner—William H. Grieb
Attorney, Agent, or Firm—Sandler, Greenblum & Bernstein

[57] ABSTRACT

A distal end part of an endoscope which is provided at the distal end of the insert part of the endoscope, comprising an illuminating window through which illuminating light is emitted, a viewing window disposed side by side with the illuminating window to take a light image into an objective optical system, and a single transparent cover continuously covering the respective surfaces of the illuminating and viewing windows, the cover being formed such that the wall thickness thereof is gradually changed at the portion thereof which extends between the illuminating and viewing windows. Accordingly, no illuminating light enters the visual field of the viewing optical system through the transparent cover and it is therefore possible to obtain a clear observation field of view which is free from a ghost or flare.

13 Claims, 8 Drawing Sheets

DISTAL END PART OF ENDOSCOPE

BACKGROUND OF THE INVENTION

1. Field of the Invention

The present invention relates to a distal end part of an endoscope. More particularly, the present invention pertains to a transparent cover that is provided at the distal end of the insert part of an endoscope to cover the respective surfaces of an illuminating window and a viewing window.

2. Description of the Related Art

A viewing window and an illuminating window are disposed side by side at the distal end of the insert part of an endoscope. The surfaces of these windows must be covered with a transparent cover so that water or other external matter will not enter the endoscope. The transparent cover has heretofore been provided independently for each of the surfaces of the viewing and illuminating windows.

Recently, the possibility that bacteria and viruses will be transferred from one patient to another through an endoscope has attracted attention and there has been an increasing need to prevent such a problem effectively and reliably.

One such effective means is to use an endoscope with its insert part being covered with a watertight sheath which enables the insert part to be removably inserted thereinto and replace the sheath with a new one after the use. In this case, that portion of the sheath which covers the surfaces of the viewing and illuminating windows must be transparent.

Figure 14:
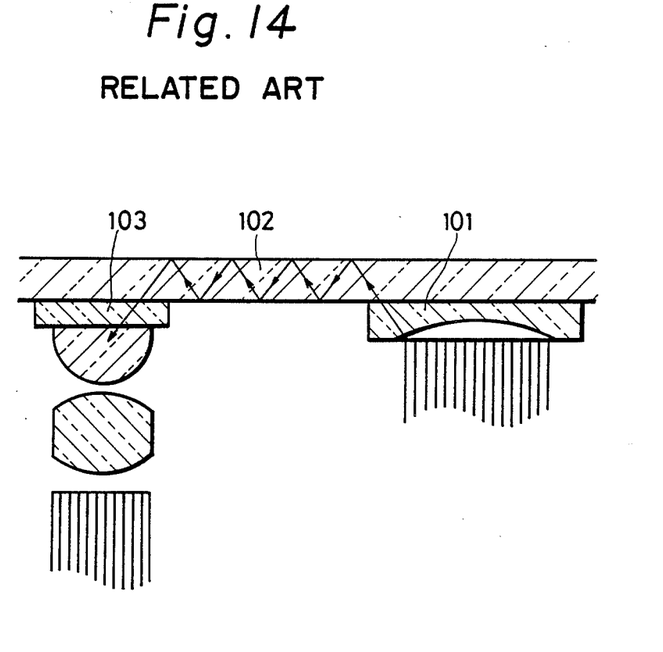
FIG. 14 is a fragmentary sectional view of a related art.

However, when the surfaces of the two windows are covered with a single continuous transparent cover, problems arise. For example, as shown in FIG. 14, a part of the illuminating light that is emitted from an illuminating window 101 enters a viewing window 103 after being repeatedly reflected within a transparent cover 102, thus causing a ghost or flare to appear in the observation field of view. Since the illuminating light that is emitted from the illuminating window of an endoscope is considerably bright, the ghost or flare thus produced is so intense that the endoscope cannot practically be used.

Theoretically, it is possible to form a cover in which those portions thereof which cover the respective surfaces of the viewing and illuminating windows are transparent, while the portion thereof which extends therebetween is opaque. However, it will be highly costly to produce such a cover that only those portions thereof which face the respective surfaces of the two windows are transparent independently of each other because of the endoscope structure in which the two windows, each having a diameter of about several millimeters, are disposed in close proximity to each other. In addition, the transparent portions of the cover may be displaced from the respective windows during use.

In the case where transparent covers are provided for the respective surfaces of the two windows as in the common practice, a light shielding black adhesive or the like must be filled in the top portion of a partition wall that partitions off the two windows from each other so that illuminating light will not enter the viewing window through the top portion of the partition wall. In this case, however, when a drop of water or the like is caught on the adhesive-filled portion, the observation field of view is disturbed. The adhesive may come off during repetitive use and, if a drop of water is attached to the exposed top portion of the partition wall, illuminating light enters the viewing window through the water drop that functions as a lens, thus causing a ghost or flare to appear in the observation field of view.

SUMMARY OF THE INVENTION

An object of the present invention is to provide a distal end part of an endoscope wherein both viewing and illuminating windows are covered with a single continuous transparent cover without the fear of a ghost or flare appearing in the observation field of view.

Other objects and advantages of the present invention will become apparent from the following detailed description of illustrated embodiments of the invention.

According to the present invention, there is provided a distal end part of an endoscope which is provided at the distal end of the insert part of the endoscope, comprising: an illuminating window through which illuminating light is emitted; a viewing window disposed side by side with the illuminating window to take a light image into an objective optical system; and a single transparent cover continuously covering the respective surfaces of the illuminating and viewing windows, the cover being formed such that the wall thickness thereof is gradually changed at the portion thereof which extends between the illuminating and viewing windows.

In addition, there is provided a distal end part of an endoscope which is provided at the distal end of the insert part of the endoscope, comprising: an illuminating window through which illuminating light is emitted; a viewing window disposed side by side with the illuminating window to take a light image into an objective optical system; and a transparent and stretchable thin film covering the two windows, the thin film being recessed between the two windows.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

The principle of the present invention will first be explained.

Figure 1:
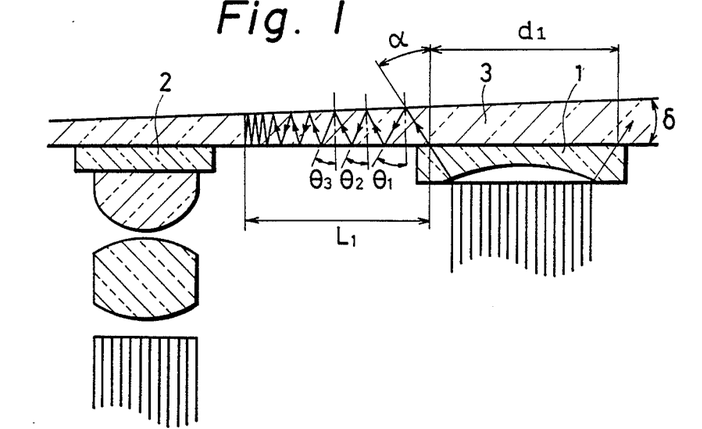
FIGS. 1 to 3 are sectional views of a distal end part of an endoscope which show the principle of the present invention.

FIG. 1 shows the way in which illuminating light travels through a transparent cover 3 which is formed such that the wall thickness thereof is gradually reduced from that portion of the cover 3 which faces the surface of an illuminating window 1 toward the portion thereof which faces the surface of a viewing window 2.

Assuming that the angle made between the upper and lower surfaces of the transparent cover 3 is $\delta$, the angle $\theta$ ($\theta_1, \theta_2 \ldots$) of reflection of the illuminating light at the upper surfaces of the transparent cover 3 decreases by $2\delta$ each time reflection occurs:

$$\theta_2 = \theta_1 - 2\delta$$

$$\theta_3 = \theta_2 - 2\delta = \theta_1 - 4\delta$$

Thus, the angle of reflection of illuminating light inside the transparent cover 3 gradually decreases and, therefore, the number of times of reflection increases considerably in comparison with the arrangement shown in FIG. 14. The illuminating light cannot travel through the transparent cover 3 in excess of a predetermined distance $L_1$.

For instance, if it is assumed that the maximum outgoing angle $\alpha$ of the illuminating light with respect to the optical axis of the illuminating light is 35°, the diameter $d_1$ of the bundle of illuminating light rays at the lower surface of the transparent cover 3 is 2.5 mm, the wall thickness of that portion of the transparent cover 3 which is disposed in front of the illuminating window 1 is 0.45 mm and $\delta$ is 2°, then the distance $L_1$ is 2.35 mm. In such a case, therefore, no illuminating light reaches the viewing window 2 if the viewing window 2 is at least 2.35 mm separated from the peripheral edge of the bundle of illuminating light rays that has the diameter $d_1$.

Further, if the angle $\delta$ made between the upper and lower surfaces of the transparent cover 3 is increased or the wall thickness of the transparent cover 3 is reduced, it is possible to shorten the distance $L_1$ and hence dispose the two windows closer to each other.

Figure 2:
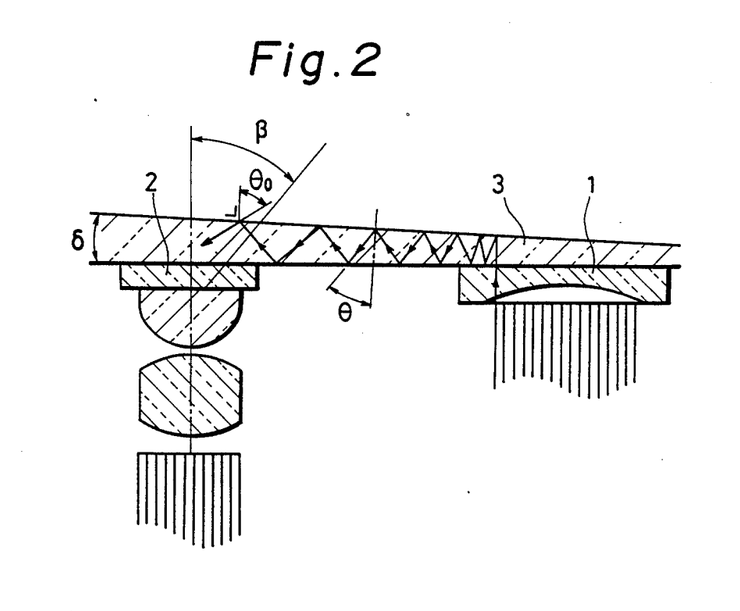

FIG. 2 shows a transparent cover 3 which is formed such that the wall thickness thereof is gradually increased from that portion of the cover 3 which faces the illuminating window 1 toward the portion thereof which faces the viewing window 2.

In this case, the angle $\theta$ of reflection of the illuminating light at the upper surface of the transparent cover 3 increases by $2\delta$ each time reflection occurs. Therefore, the illuminating light reaches that portion of the transparent cover 3 which faces the viewing window 2. However, as long as the incident angle ($\theta_0 + \delta$) of the illuminating light to the viewing window 2 is greater than the maximum incident angle $\beta$ of the viewing optical system, no illuminating light enters the observation field of view, so that neither ghost nor flare appears. To attain the condition of $\theta_0 + \delta > \beta$, it is only necessary that the number of times of reflection of the illuminating light at the inner surfaces of the transparent cover 3 be increased and the distance between the illuminating and viewing windows 1 and 2 be greater than a predetermined value.

Figure 3:
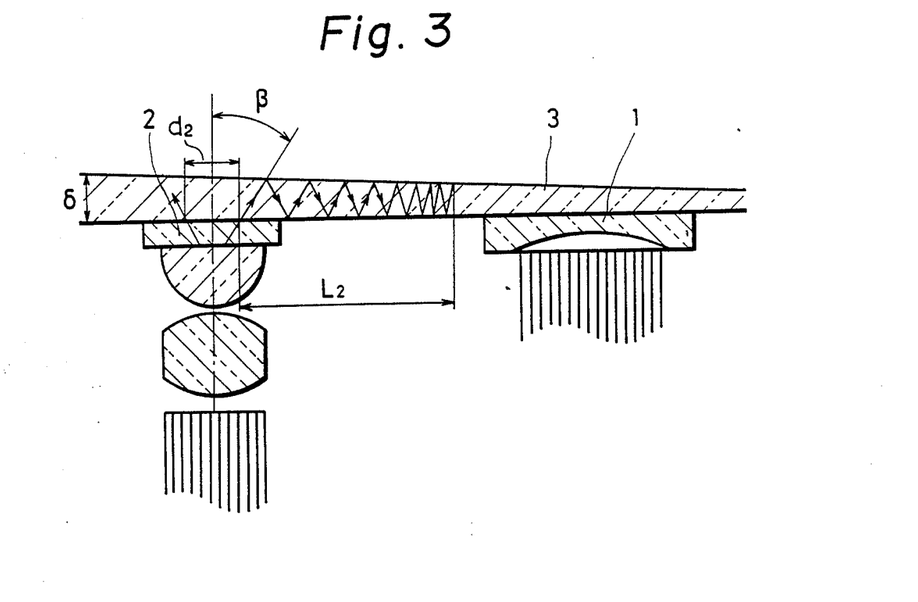

The distance between the two windows may be obtained by tracing backward the reflected ray from the side of the transparent cover 3 which is closer to the viewing window 2, as shown in FIG. 3. More specifically, the reflection angle of the ray of light that starts to reflect within the transparent cover 3 at the same angle as the maximum incident angle $\beta$ of the viewing optical system gradually decreases as the reflected light travels in the direction in which the wall thickness of the cover 3 gradually decreases, so that the light cannot travel more than the distance $L_2$ from the optical axis of the viewing optical system.

For instance, if it is assumed that the maximum incident angle $\beta$ of the viewing optical system is 35°, the diameter $d_2$ of the bundle of viewing light rays at the lower surface of the transparent cover 3 is 0.8 mm, the wall thickness of that portion of the transparent cover 3 which is disposed in front of the viewing window 2 is 0.45 mm and $\delta$ is 2°, then the distance $L_2$ is 2.35 mm. Thus, no illuminating light enters the viewing window 2 if the illuminating window 1 is at least 2.35 mm separated from the peripheral edge of the bundle of viewing light rays that has the diameter $d_2$.

In this case also, it is possible to shorten the distance $L_2$ by increasing the angle $\delta$ made between the upper and lower surfaces of the transparent cover 3 or reducing the thickness of the cover 3.

Figure 4:
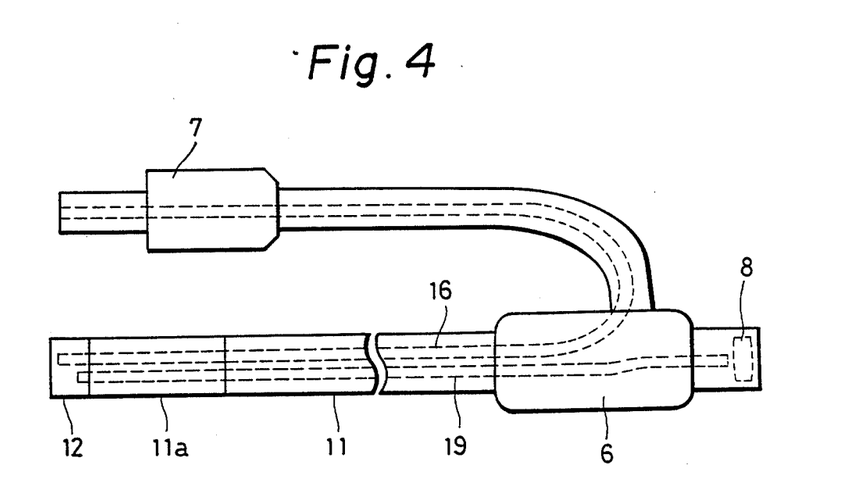
FIG. 4 is a schematic view of an endoscope to which one embodiment of the present invention is applied.

FIG. 4 shows an endoscope to which one embodiment of the present invention is applied. In the figure, the reference numeral 11 denotes a flexible tube with which the insert part of the endoscope is sheathed, while the numeral 12 denotes a distal end unit that is connected to the distal end of the flexible tube 11. That portion of the flexible tube 11 which is adjacent to the distal end unit 12 is defined as a bendable portion 11a which is bendable by a remote control. The reference numeral 6 denotes a control part. The numeral 7 denotes a connector which is connected to a light source device. The reference numeral 8 denotes an ocular lens. A light guide fiber bundle 16 and an image guide fiber bundle 19 are received in the endoscope. One end of the image guide fiber bundle 19 is disposed so as to face the ocular lens 8. Illuminating light is made incident on the end face of the light guide fiber bundle 16 which is closer to the connector 7.

Figure 5:
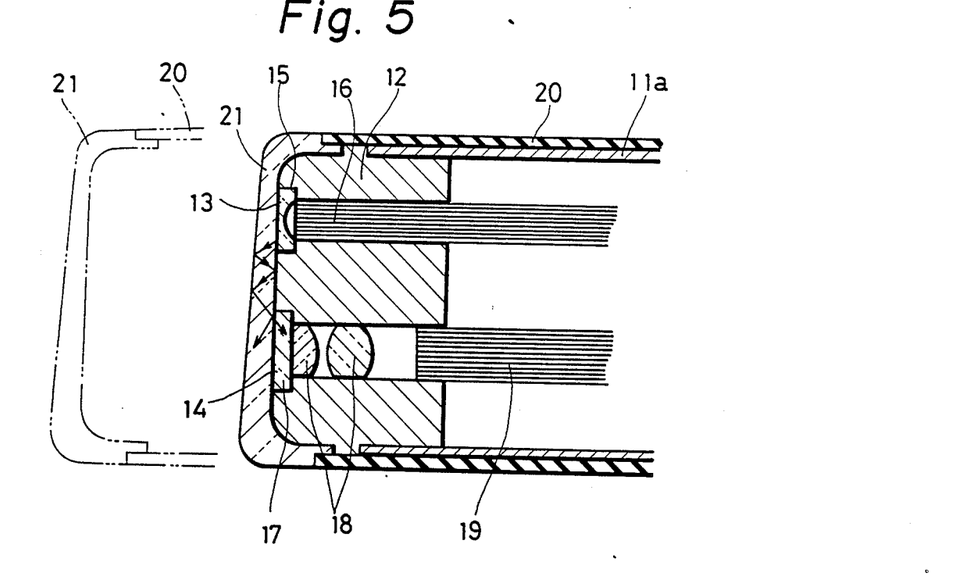
FIG. 5 is a sectional view of the distal end part of the endoscope according to the embodiment of the present invention.

FIG. 5 shows the distal end part of the endoscope.

An illuminating window 13 for emitting illuminating light and a viewing window 14 for taking a light image into an objective optical system are provided in the forward end face of the distal end part 12, the two windows being disposed side by side and facing forward. A concave lens 15 is fitted in the illuminating window 13, and the emergent end portion of the light guide fiber bundle 16 is disposed at the rear of the concave lens 15. A cover glass 17 is fitted in the viewing window 14, and objective lenses 18 and the incident end portion of the image guide fiber bundle 19 are disposed at the rear of the cover glass 17.

The reference numeral 20 denotes a tubular flexible sheath. A transparent cover 21 which is made of a transparent plastic material, for example, an acrylic plastic material, is attached to the distal end of the sheath 20 in such a manner that no water or the like leaks in through the joint of the cover 21 and the sheath 20. The insert part that has the illuminating and viewing windows 13 and 14 provided in the distal end unit 12 side by side with each other is removably inserted into the flexible sheath 20. The flexible sheath 20 that is forwardly drawn out from the insert part is shown by the two-dot chain line in FIG. 5. When the insert part of the endoscope is fully inserted into the sheath 20, the concave lens 15 fitted in the illuminating window 13 and the cover glass 17 fitted in the viewing window 14 are in close contact with the transparent cover 21, as shown by the solid line.

The transparent cover 21 is formed such that the wall thickness thereof is gradually increased from that portion of the cover 21 which faces the illuminating window 13 toward the portion thereof which faces the viewing window 14.

In the distal end part of the endoscope arranged as described above, a part of the illuminating light emitted from the light guide fiber bundle 16 is repeatedly reflected inside the transparent cover 21. Each time the light is reflected, the angle of reflection of the illuminating light gradually increases and, at the position that faces the viewing window 14, the reflection angle is greater than the maximum incident angle of the objective lenses 18 and, therefore, no illuminating light enters the observation field of view.

It should be noted that the transparent cover 21 may be formed such that the wall thickness thereof is gradually reduced from that portion of the cover 21 which faces the illuminating window 13 toward the portion thereof which faces the viewing window 14, as has already been described in connection with FIG. 1.

Figure 6:
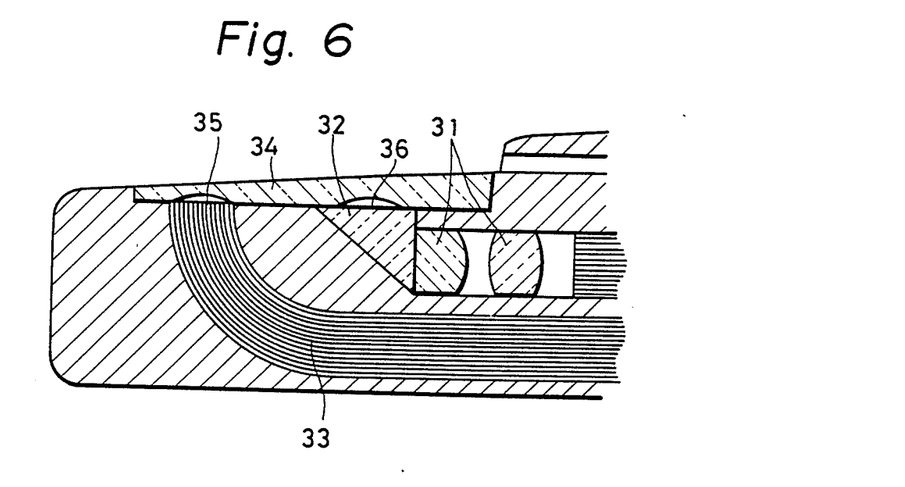
FIG. 6 is a fragmentary sectional view of another embodiment of the present invention.

FIG. 6 shows a second embodiment of the present invention in which the present invention is applied to a side-viewing endoscope. In this embodiment, a single transparent cover glass 34 is provided in such a manner that the cover glass 34 is in contact with both the end face of a rectangular roof prism 32 disposed in front of objective lenses 31 and the emergent end face of a light guide fiber bundle 33. In this embodiment, the emergent end portion of the light guide fiber bundle 33 forms an illuminating window 35, while the outer end portion of the prism 32 forms a viewing window 36, and the transparent cover glass 34 covers the surfaces of these windows 35 and 36.

Those portions of the reverse surface of the transparent cover glass 34 which face the windows 35 and 36, respectively, are formed in the shape of concave surfaces so that the angle of distribution of illuminating light and the angle of observation field are enlarged at these portions.

The transparent cover glass 34 is formed such that the wall thickness thereof is gradually increased from the side of the cover glass 34 which is closer to the illuminating window 35 toward the side thereof which is closer to the viewing window 36, thereby preventing the illuminating light from entering the observation field of view, in the same way as in the above-described first embodiment. If the illuminating and viewing windows 35 and 36 are covered directly with a single cover glass as in the case of this embodiment, there is no step or the like between the two windows 35 and 36 and, therefore, drops of water or the like flow smoothly without being caught on the surface of the cover glass. Thus, it is possible to obtain an excellent field of view.

Figure 7:
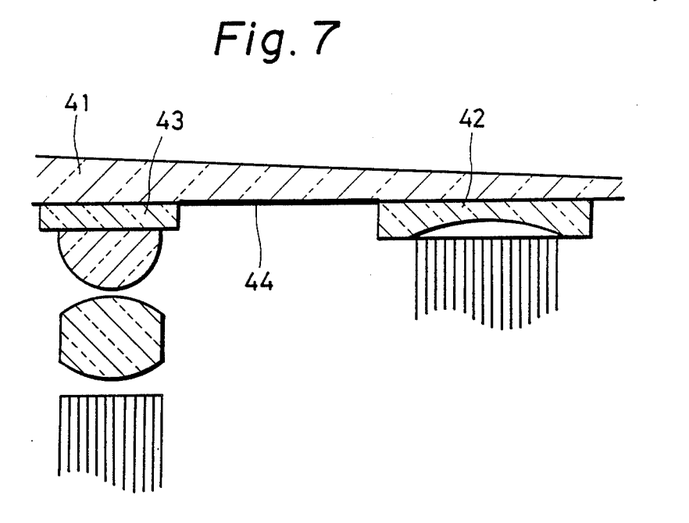
FIGS. 7 and 8 are fragmentary sectional views each showing a further embodiment of the present invention in which an antireflection surface is provided.

FIG. 7 shows a further embodiment of the present invention in which an antireflection surface 44 which reduces reflection of light is provided on a portion of the reverse surface of a transparent cover 41 which extends between an illuminating window 42 and a viewing window 43. The antireflection surface 44 is, for example, a black-painted surface. The antireflection surface 44 enables the illuminating light traveling through the transparent cover 41 to be attenuated by a large margin before reaching that portion of the transparent cover 41 which faces the viewing window 43. The antireflection surface 44 is formed on a portion of the transparent cover 41 other than the two optical paths, that is, the illuminating light path and the viewing light path. The antireflection surface 44 may be formed on either the upper or lower surface or both the upper and lower surfaces of the transparent cover 41.

Figure 8:
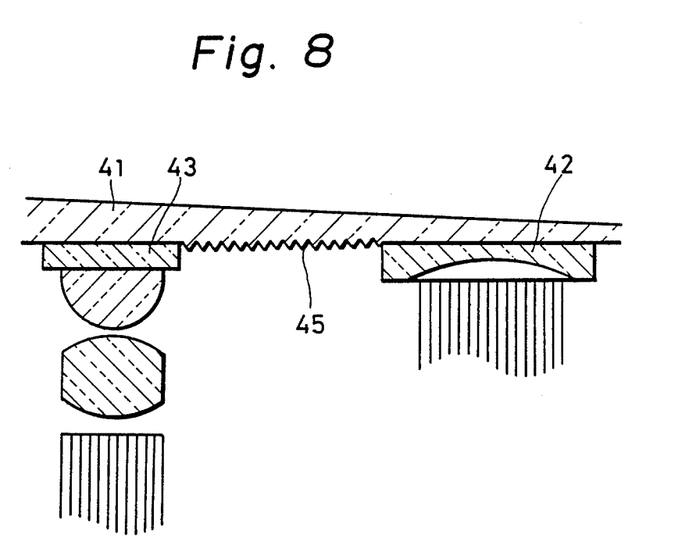

FIG. 8 shows an arrangement in which a multiplicity of narrow grooves (or a multiplicity of minute projections and recesses) 45 are formed to constitute an antireflection surface. These grooves 45 enable the reflected light to be directly cut off. If the grooves 45 are painted in black, the reflected light can be cut off even more effectively.

Figure 9:
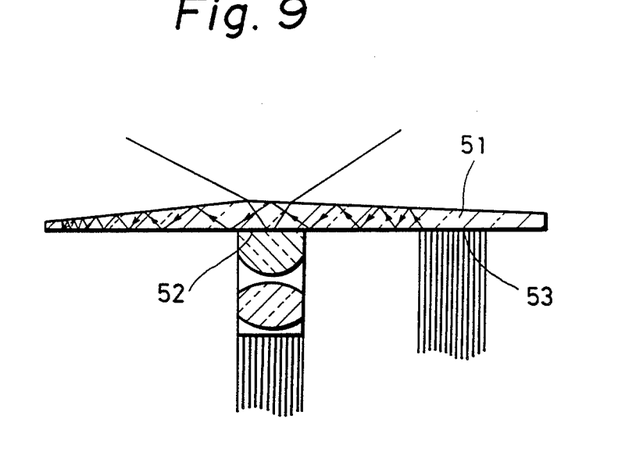
FIGS. 9 and 10 are fragmentary sectional views each showing a still further embodiment of the present invention in which the transparent cover has the largest wall thickness at the portion thereof which faces the viewing window.

FIG. 9 shows a further embodiment of the present invention in which the wall thickness of a transparent cover 51 is the largest at that portion thereof which faces a viewing window 52 and is gradually reduced toward the periphery from the thickest portion. By virtue of this arrangement, the reflection angle of the illuminating light that travels through the transparent cover 51 gradually decreases after the light has passed the front of the viewing window 52 and the travel of the light eventually stops. There is therefore no possibility that the illuminating light that has passed the front of the viewing window 52 will return to the viewing window 52 by reflection. Thus, it is possible to obtain an observation field of view with a good contrast. The reference numeral 53 denotes an illuminating window.

Figure 10:
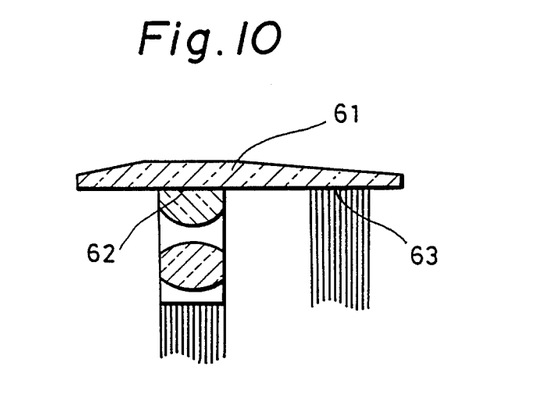

FIG. 10 shows a further embodiment of the present invention in which a transparent cover 61 having an arrangement similar to that shown in FIG. 9 is employed and only the portion thereof which faces a viewing window 62 is formed in a plane-parallel structure. This arrangement enables realization of a viewing optical system in which the optical axis of the viewing light path has no inclination. The reference numeral 63 denotes an illuminating window.

According to the present invention, both the viewing and illuminating windows are covered with a single transparent cover the wall thickness of which is gradually changed. It is therefore possible to reduce the production cost of the distal end part of an endoscope and also prevent the illuminating light from entering the visual field of the viewing optical system through the transparent cover with an extremely simple structure. Thus, it is possible to obtain a clear observation field of view which is free from a ghost or flare. Since there is no step or the like between the viewing and illuminating windows, no drop of water or the like is caught on that portion of the transparent cover which extends between the viewing and illuminating windows. Accordingly, it is possible to obtain an excellent field of view.

Figure 11:
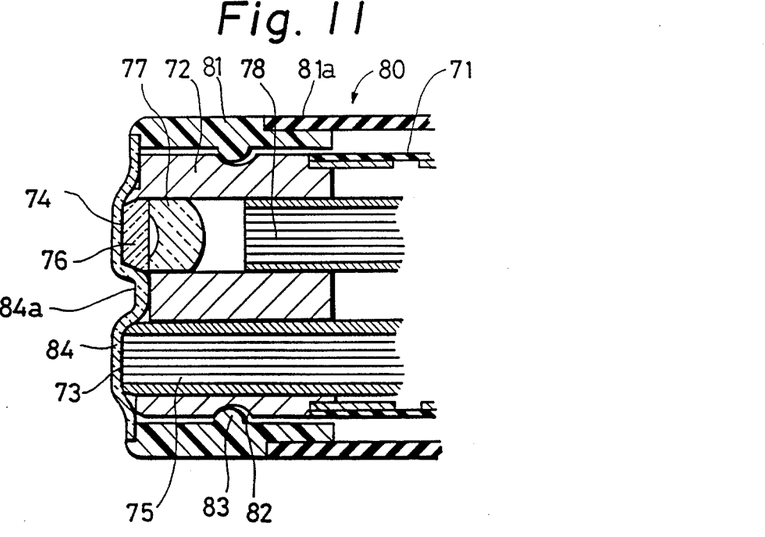
FIG. 11 is a sectional side view of a still further embodiment of the present invention.

FIG. 11 shows another embodiment of the present invention. In the figure, the reference numeral 71 denotes a flexible tube with which the insert part of the endoscope is sheathed, while the numeral 72 denotes a distal end unit that is connected to the distal end of the flexible tube 71. That portion of the flexible tube 71 which is adjacent to the distal end unit 72 is defined as a bendable portion which is bendable by a remote control (detailed illustration thereof being omitted). An illuminating window 73 for emitting illuminating light and a viewing window 74 for taking a light image into an objective optical system are provided in the forward end face of the distal end part 72, the two windows being disposed side by side and facing forward. The illuminating and viewing windows 73 and 74 project from the distal end unit 72 independently of each other. The emergent end portion of a light guide fiber bundle 75 is disposed at the rear of the illuminating window 73, while a cover glass 76 is fitted in the viewing window 74. An objective lens 77 and the incident end portion of an image guide fiber bundle 78 are disposed at the rear of the viewing window 74.

The reference numeral 80 denotes a tubular sheath which enables the flexible tube 71 to be removably inserted thereinto. That portion of the sheath 80 which is fitted on the outer peripheral portion of the distal end unit 72 is constituted by a relatively rigid tubular member 81, and a flexible, non-rigid tube 81a is connected to the rear end of the tubular member 81. The tubular member 81 has a click 83 projecting from the inner surface thereof, the click 83 being engageable with a click groove 82 which is formed in the outer surface of the distal end unit 72. By engagement of the click 83 with the click groove 82, the distal end unit 72 and the tubular member 81 are connected together with a predetermined positional relation to each other.

A single transparent and stretchable thin film 84 which is made of a synthetic resin material, for example, polypropylene, polyethylene, etc., is attached to the forward end of the tubular member 81 in such a manner that no water or the like leaks in through the joint of the thin film 84 and the tubular member 81. The wall thickness of the transparent thin film 84 is, for example, from about 0.05 mm to about 0.5 mm. When the click 83 and the click groove 82 are in engagement with each other, the two windows 73 and 74 are pressed against the transparent thin film 84. As a result, the transparent thin film 84 is tensely brought into close contact with the surfaces of the windows 73 and 74. The transparent thin film 84 is asymmetrically recessed toward the distal end unit 72 at the area between the two windows 73 and 74, as denoted by the reference numeral 84a. The depth of the recess 84a is preferably about two to five times the wall thickness of the transparent thin film 84.

In the embodiment having the above-described arrangement, a part of the illuminating light emitted outward from the illuminating window 73 travels through the transparent thin film 84 while being repeatedly reflected therein in the same way as in the prior art. However, since the transparent thin film 84 is recessed between the two windows 73 and 74, the optical path of the light that passes through the recess 84a is markedly extended, so that the transmittance of the light that reaches the viewing window 74 lowers.

Figure 12:
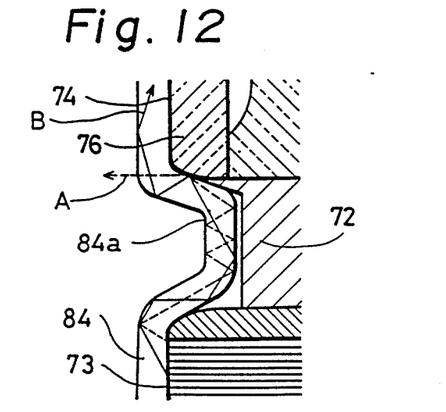
FIG. 12 is an enlarged view of an essential part of the embodiment shown in FIG. 11.

Since the recess 84a is asymmetric, a part of the illuminating light that is transmitted by the film 84 while being reflected therein changes its course during the travel through the recess 84a and therefore the greater part of the light comes out of the film 84, as shown by the chain line A in FIG. 12, or becomes a light ray having such an angle that it will not enter the viewing window 74, as shown by the solid line B. In addition, since the film 84 is thin, the illuminating light that is transmitted by the film 84 is reflected therein a considerably large number of times. Accordingly, even if a part of the illuminating light reaches the viewing window 74, the intensity of the light has already attenuated through the repetition of reflection to such a level that there is no practical problem on the image for observation.

Since the transparent thin film 84 is in close contact with the two windows 73 and 74 while being on the stretch, there is no fear of irregular reflection occurring between each of the windows 73 and 74 and the transparent thin film 84 and there will be no distortion of the image.

Figure 13:
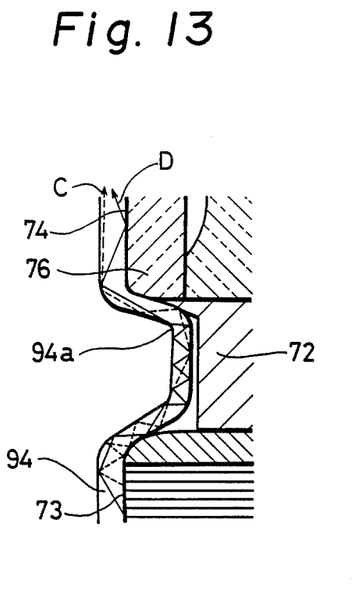
FIG. 13 is a sectional side view of a still further embodiment of the present invention.

FIG. 13 shows still another embodiment of the present invention in which the wall thickness of the transparent thin film 94 is reduced at the asymmetric recess 94a. Such a thin-walled portion may be formed by tightly stretching the transparent thin film 94. It is also possible to use a transparent thin film originally formed with such a thin-walled portion. By virtue of this arrangement, the greater part of the light becomes light rays having such an angle that they will not enter the viewing window 74, as shown by the chain and solid lines C and D in FIG. 13.

It should be noted that a plurality of recesses 84a or 94a may be formed in the foregoing embodiments.

Thus, according to the present invention, the greater part of the illuminating light entering the transparent thin film comes out of the film at the recessed portion thereof or becomes light rays having such an angle that they will not enter the viewing window. Accordingly, substantially no light enters the viewing window. Even if a part of the illuminating light reaches the viewing window, the intensity thereof has already weakened through the repetition of reflection occurring inside the transparent thin film, so that no ghost or flare which disturbs the observation will appear. In addition, since the transparent thin film is in close contact with the two windows while being stretched, there is neither irregular reflection between the windows and the transparent thin film nor distortion of the image. It is therefore possible to obtain a clear image for observation. Since the distal end part of the present invention is extremely inexpensive, it may be disposable.

While the invention has been described by reference to specific embodiments chosen for purposes of illustration, it should be apparent that numerous modifications could be made thereto by those skilled in the art without departing from the basic concept and scope of the invention.

What is claimed is:

1. A distal end part of an endoscope which is provided at the distal end of the insert part of said endoscope, comprising:
   an illuminating window through which illuminating light is emitted;
   a viewing window for taking a light image into an objective optical system; and
   a transparent cover continuously covering the respective surfaces of said illuminating and viewing windows, said cover being formed such that the wall thickness thereof is gradually changed at the portion thereof which extends between said illuminating and viewing windows.

2. A distal end part of an endoscope according to claim 1, wherein the wall thickness of said transparent cover is gradually increased from that portion of said cover which faces the surface of said illuminating window toward the portion thereof which faces the surface of said viewing window.

3. A distal end part of an endoscope according to claim 1, wherein the wall thickness of said transparent cover is gradually reduced from that portion of said cover which faces the surface of said illuminating window toward the portion thereof which faces the surface of said viewing window.

4. A distal end part of an endoscope according to claim 1, wherein said transparent cover is attached to the distal end of a tubular sheath which is designed so that said distal end part having said illuminating and viewing windows disposed therein side by side can be inserted into and removed from said sheath as desired.

5. A distal end part of an endoscope according to claim 1, wherein the reverse surface of said transparent cover is formed so as to be concave at at least one portion thereof which covers either the surface of said illuminating window or the surface of said viewing window.

6. A distal end part of an endoscope according to claim 1, wherein an antireflection means for reducing reflection of light is provided on a portion of the reverse surface of said transparent cover which extends between said illuminating and viewing windows.

7. A distal end part of an endoscope according to claim 6, wherein said antireflection means is a black-painted surface.

8. A distal end part of an endoscope according to claim 6, wherein said antireflection means is constituted by a multiplicity of narrow grooves.

9. A distal end part of an endoscope according to claim 1, wherein the wall thickness of said transparent cover is the largest at that portion thereof which faces the surface of said viewing window and is gradually reduced toward the periphery from said thickest portion.

10. A distal end part of an endoscope according to claim 9, wherein that portion of said transparent cover which faces the surface of said viewing window is formed in a plane-parallel structure.

11. A distal end part of an endoscope which is provided at the distal end of the insert part of said endoscope, comprising:
an illuminating window through which illuminating light is emitted;
a viewing window disposed side by side with said illuminating window to take a light image into an objective optical system; and
a transparent and stretchable film covering said two windows, said film being curved between said two windows.

12. A distal end part of an endoscope according to claim 11, wherein said two windows project from said distal end part, said thin film being disposed in close contact with the respective surfaces of said two windows, and said film being asymmetrically recessed between said two windows.

13. A distal end part of an endoscope according to claim 11, wherein the wall thickness of said transparent thin film is smaller at said recessed portion than at those portions thereof which cover the respective surfaces of said two windows.

* * * * *